US006837243B1

(12) United States Patent
Fetters

(10) Patent No.: US 6,837,243 B1
(45) Date of Patent: Jan. 4, 2005

(54) AUTOMATIC TRANSFER REGULATOR FOR HOSE-LINE RESPIRATOR

(75) Inventor: Thomas Allen Fetters, Fort Mill, SC (US)

(73) Assignee: Scott Technologies, Inc., Beachwood, OH (US)

( * ) Notice: Subject to any disclaimer, the term of this patent is extended or adjusted under 35 U.S.C. 154(b) by 0 days.

(21) Appl. No.: 10/675,069

(22) Filed: Sep. 30, 2003

(51) Int. Cl.$^7$ ............................................... F16K 31/26
(52) U.S. Cl. .................... 128/204.26; 128/200.24; 128/204.18; 128/205.18; 128/205.22; 128/205.23; 128/205.24; 128/205.25
(58) Field of Search ................. 128/204.26, 205.24, 128/205.18, 205.22, 205.25, 205.23

(56) References Cited

U.S. PATENT DOCUMENTS

| | | | |
|---|---|---|---|
| 2,408,799 A | | 10/1946 | Melichar |
| 3,456,642 A | | 7/1969 | Cupp |
| 3,481,356 A | | 12/1969 | McQueen |
| 3,508,542 A | | 4/1970 | Browner |
| 3,742,972 A | | 7/1973 | Hughes |
| 3,744,526 A | | 7/1973 | MacNiel |
| 3,957,044 A | | 5/1976 | Fletcher et al. |
| 4,067,354 A | | 1/1978 | St. Clair |
| 4,067,355 A | | 1/1978 | St. Clair |
| 4,108,171 A | * | 8/1978 | Nyman et al. ......... 128/202.14 |
| 4,141,356 A | * | 2/1979 | Smargiassi ............. 128/204.23 |
| 4,279,250 A | * | 7/1981 | Valenta et al. ......... 128/200.14 |
| 4,619,255 A | | 10/1986 | Spinosa et al. |
| 4,651,728 A | | 3/1987 | Gupta et al. |
| 5,022,393 A | | 6/1991 | McGrady et al. |
| 5,072,728 A | * | 12/1991 | Pasternack ............. 128/204.18 |
| 5,076,267 A | * | 12/1991 | Pasternack ............. 128/205.22 |
| 5,156,145 A | | 10/1992 | Flood et al. |
| 5,165,625 A | | 11/1992 | Gutman |
| 5,293,864 A | | 3/1994 | McFadden |
| 5,318,019 A | | 6/1994 | Celaya |
| 5,357,949 A | | 10/1994 | Bertheau et al. |
| 5,368,018 A | * | 11/1994 | Stone ..................... 128/201.28 |
| 5,368,020 A | * | 11/1994 | Beux ..................... 128/204.29 |
| 5,467,766 A | | 11/1995 | Ansite et al. |
| 5,542,447 A | | 8/1996 | Foote et al. |
| 5,603,315 A | * | 2/1997 | Sasso, Jr. .............. 128/204.18 |
| 5,642,729 A | | 7/1997 | Cassidy |
| 5,730,121 A | | 3/1998 | Hawkins, Jr. et al. |
| 5,794,615 A | * | 8/1998 | Estes ..................... 128/204.23 |
| 5,803,065 A | * | 9/1998 | Zdrojkowski et al. . 128/204.23 |
| 5,813,399 A | * | 9/1998 | Isaza et al. ............ 128/204.21 |
| 5,813,400 A | * | 9/1998 | Buhlmann et al. ..... 128/204.23 |
| 5,865,174 A | * | 2/1999 | Kloeppel ............... 128/204.23 |
| 5,924,418 A | * | 7/1999 | Lewis .................... 128/204.22 |
| 5,954,051 A | * | 9/1999 | Heinonen et al. ...... 128/205.24 |
| 6,029,660 A | * | 2/2000 | Calluaud et al. ....... 128/203.12 |
| 6,029,664 A | * | 2/2000 | Zdrojkowski et al. . 128/204.23 |
| 6,035,891 A | | 3/2000 | Hawkins, Jr. et al. |

(List continued on next page.)

FOREIGN PATENT DOCUMENTS

DE              152622           10/1937

*Primary Examiner*—Henry Bennett
*Assistant Examiner*—Nihir Patel
(74) *Attorney, Agent, or Firm*—Hodgson Russ LLP

(57) ABSTRACT

An automatic transfer regulator for automatically switching between a primary (hose line) breathing air source and a secondary source (escape cylinder). A pressure sensing system detects the line pressure of the primary source using a spring loaded poppet connected to one side of a transfer poppet valve, with the other side connected to the output of a reducer. The pressure sensing system is fed by the primary source through an orifice. When the sensor detects loss of hose line pressure, the system pressure is released to ambient. This bleeds the pressure from the system side of the transfer poppet valve, allowing the reducer output to force the poppet back, thus actuating the secondary source. A check valve prevents reducer output from escaping through the primary source inlet.

29 Claims, 1 Drawing Sheet

U.S. PATENT DOCUMENTS

| | | | | |
|---|---|---|---|---|
| 6,089,229 A | * | 7/2000 | Bathe et al. | 128/204.21 |
| 6,125,846 A | * | 10/2000 | Bathe et al. | 128/202.22 |
| 6,142,147 A | * | 11/2000 | Head et al. | 128/204.21 |
| 6,152,129 A | * | 11/2000 | Berthon-Jones | 128/200.24 |
| 6,158,434 A | * | 12/2000 | Lugtigheid et al. | 128/204.22 |
| 6,164,276 A | * | 12/2000 | Bathe et al. | 128/202.22 |
| 6,170,483 B1 | * | 1/2001 | Ronjat | 128/201.27 |
| 6,173,711 B1 | * | 1/2001 | Ruton | 128/204.26 |
| 6,237,594 B1 | * | 5/2001 | Davenport | 128/204.26 |
| 6,244,267 B1 | * | 6/2001 | Eifrig | 128/202.22 |
| 6,378,520 B1 | * | 4/2002 | Davenport | 128/204.26 |
| 6,401,714 B1 | * | 6/2002 | Giorgini | 128/204.26 |
| 6,427,689 B1 | * | 8/2002 | Estes et al. | 128/204.18 |
| 6,622,726 B1 | * | 9/2003 | Du | 128/204.26 |
| 6,651,658 B1 | * | 11/2003 | Hill et al. | 128/204.23 |
| 6,675,798 B1 | * | 1/2004 | Tyomkin et al. | 128/204.23 |
| 6,701,923 B2 | * | 3/2004 | Cazenave et al. | 128/204.22 |
| 6,709,405 B2 | * | 3/2004 | Jonson | 600/538 |
| 6,712,071 B1 | * | 3/2004 | Parker | 128/204.21 |
| 6,718,975 B2 | * | 4/2004 | Blomberg | 128/204.23 |

* cited by examiner

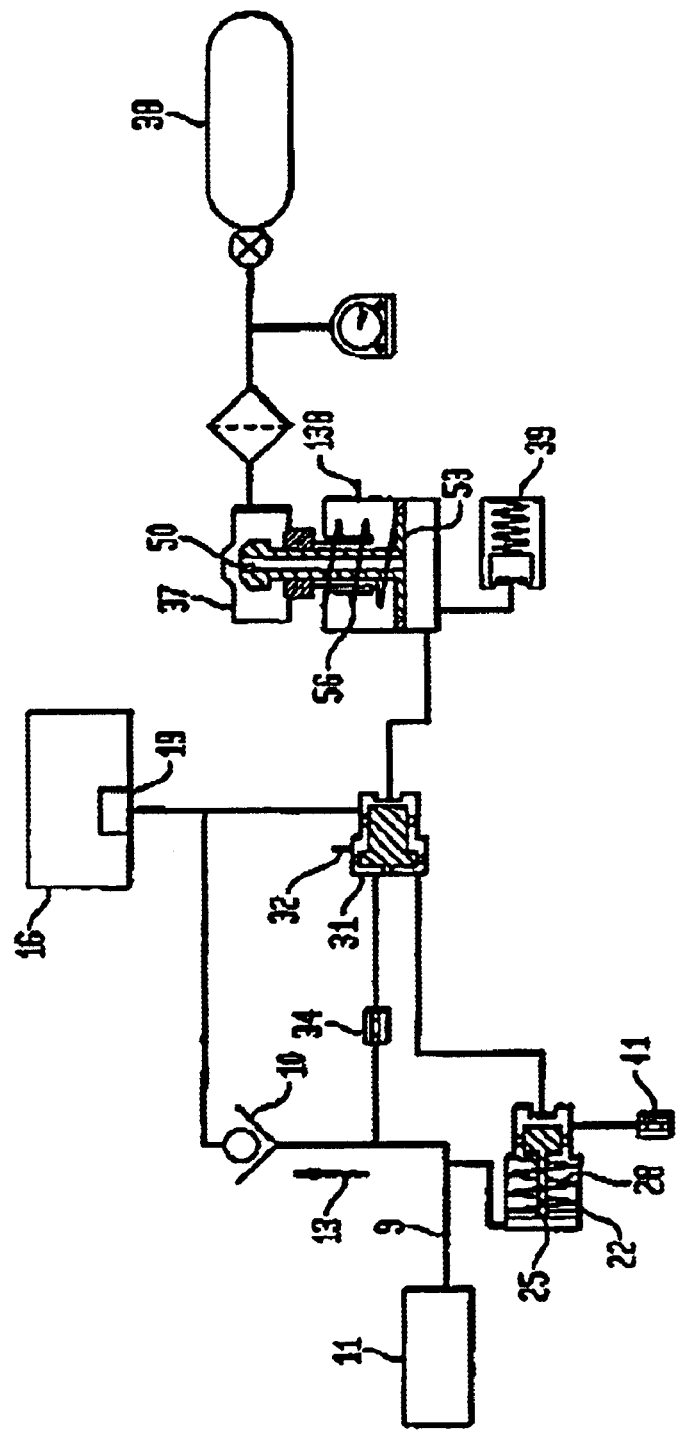

AUTOMATIC TRANSFER REGULATOR FOR HOSE-LINE RESPIRATOR

FIELD OF INVENTION

The present invention relates to a system for providing breathing air, under life-threatening emergency conditions, to a user otherwise trapped in a non-breathable atmosphere.

BACKGROUND OF THE INVENTION

The use of breathing devices in non-breathable atmospheres is well known. In some instances, self-contained breathing apparatus ("SCBA") may be utilized to provide breathing air to the user. In other situations, a hose-line respirator connected to a remote air source is utilized. The hose-line respirator may be used in situations where workers are required to work for a long period of time in an atmosphere containing a hazardous substance. Also, the hose line respirator may be used if there is not enough room for a larger tank to be carried into the work area. For the above reasons and others, it is sometimes preferable to use a hose-line connected between the user's breathing mask and a remote large source of breathable gas.

When a hose-line respirator attached to a remote supply of breathing gas is utilized, there is a need for an emergency escape respirator. The need arises because the remote breathing gas supply may fail. For example, the hose line may become uncoupled from the breathing gas source. Also, the hose may be accidentally damaged or even severed between the breathing mask and the breathing gas supply.

Some escape systems require at least some conscious participation by the user or other person, a requirement which may not be feasible in a sudden emergency situation where the user is restrained by being trapped or otherwise disoriented, unconscious or so stricken as to be unable to think or act appropriately. For example, a small supply of compressed air is carried on the person and is connected by a Tee into the air supply line. If the air supply through the hose line should fail, the worker is instructed to open the valve of his reserve air supply and immediately leave the area. In order to make such a device practical, the air from the reserve cylinder is first run through a regulator to reduce its pressure. A check valve is also incorporated to prevent the air from the emergency supply traveling down the hose towards the original air supply.

Accordingly, there is a need for a transfer regulator capable of automatically switching the breathing gas supply from the hose-line to a portable emergency tank when the flow of breathing gas through the hose-line is disrupted. There is also a need for a system that automatically resets itself when the supply of breathing gas from the remote source is restored.

SUMMARY OF THE INVENTION

The present invention meets the above-described needs by providing an apparatus for providing breathing gas in an emergency situation. The primary air supply source is continuous, pressurized breathable air from a source such as a remotely located, large air cylinder or the like which supplies breathable gas to the user through a hose. The secondary breathing gas source comprises a limited capacity compressed gas source, such as a small escape cylinder or the like, which comprises an emergency supply of breathable gas, for example approximately ten minutes worth of supply. The secondary breathing gas source is interconnected with the primary source and is generally carried by and/or is conveniently mounted on the user.

The primary breathing gas is delivered at a first operative pressure through a hose line to a regulator on the breathing mask worn by the user. The secondary breathing gas is maintained at a second operative pressure that is higher than the first operative pressure.

The automatic transfer regulator of the present invention provides for automatically switching between the primary (hose line) breathing air source and the secondary source (escape cylinder). A pressure sensing system detects the line pressure of the primary source using a spring loaded poppet connected to one side of a transfer poppet valve, with the other side connected to the output of a reducer. The pressure sensing system is fed by the primary source through an orifice. When the sensor detects loss of hose line pressure, the system pressure is released to ambient. This bleeds the pressure from the system side of the transfer poppet valve, allowing the reducer output to force the poppet back, thus actuating the secondary source. A check valve prevents reducer output from escaping through the primary source inlet.

BRIEF DESCRIPTION OF THE DRAWINGS

The sole FIGURE is a schematic illustration of a system of the present invention.

DETAILED DESCRIPTION

Referring to the FIGURE, under normal operation breathing gas at a first operative pressure of, for example, 80 to 115 psi flows in a hose line 9 from a remote breathing gas supply source 11 through a check valve 10 in the direction of arrow 13 to a breathing air mask 16. The remote supply source 11 may comprise any vessel suitable for storing breathing gas under pressure. The tank pressure is typically reduced by a primary regulator down to the line pressure set forth above. As will be evident to those of ordinary skill in the art, the mask 16 is provided with a mask mounted, demand-type or pressure demand-type regulator 19 that reduces the pressure to a breathable range. The hose line 9 is also disposed in fluid communication with a first poppet valve 22. Although a poppet valve is shown, it will be evident to those of ordinary skill that other types of pressure responsive valves may also be used. The force of the gas pressure pushes the poppet 25 to the right with respect to FIG. 1. A spring 28 is biased against the poppet 25 and urges the poppet 25 to the left with respect to FIG. 1. When the hose-line pressure is in its normal range, the poppet 25 is normally closed, and the hose line gas pressure overcomes the force of the spring 28 to keep the first poppet valve 22 closed.

Gas from the hose line 9 is also in fluid communication with the back or system side of a transfer poppet valve 31 through a 250 cc/min. flow restrictor 34. The transfer valve 31 is biased in the normally closed position and includes a static vent 32. As will be evident to those of ordinary skill in the art, other pressure responsive valves may also be utilized. The transfer poppet valve 31 is in fluid communication with the mask 16 and a pressure reducer 37. The pressure reducer 37 converts air from the escape cylinder 38 at cylinder pressure to an intermediate operating pressure of approximately 155 psi as described in greater detail below. The pressure reducer 37 also includes a static vent 138. When the transfer poppet valve 31 opens, the air from the outlet of the reducer 37 is allowed to flow to the breathing mask.

In the normally closed position of the first poppet valve 22, the air pressure from the hose line 9 through the 250 cc/min. flow restrictor 34 holds the transfer valve 31 in the closed position such that air from the reducer 37 attached to the escape cylinder 38 cannot pass through the transfer poppet valve 31.

Because of the spring bias against the poppet 25 of the first poppet valve 22, at some point a reduction in hose line pressure will cause the poppet 25 to move to the left with respect to FIG. 1 and a pathway to a 1000 cc/min. flow restrictor 41 will be opened. The opening of the flow restrictor 41 to atmosphere causes a reduction in pressure from the back side of the transfer valve 31 because the air will flow faster through the 1000 cc/min. flow restrictor 41 than it can enter through the 250 cc/min. flow restrictor 34. Accordingly, the pressure on the back side of the transfer valve 31 will eventually be unloaded such that the transfer valve 31 will open.

Once the transfer valve 31 is opened, the breathing air from the escape cylinder 38 via the reducer 37 will start to flow to the mask 16. The air from the escape cylinder 38 is reduced from bottle pressure to approximately 155 psi by the reducer 37.

The breathing air from the escape cylinder 38 flows to the mask-mounted demand type regulator 19. In certain circumstances this pressure which is maintained at a level higher than normal primary pressure may be used to trigger an alarm. This alarm may be mounted in or on the mask, the breathing regulator, or other part of the respirator connected to the breathing circuit to alert the user that the system has switch over to the escape cylinder. The check valve 10 prevents the breathing gas from escaping through hose line 9. The use of an increase in the pressure of air supplied to the facepiece mounted breathing regulator 19 in order to activate an alarm is disclosed in U.S. Pat. No. 3,975,044 which is incorporated herein by reference. U.S. Pat. No. 3,975,044 is assigned to Scott Technologies, Inc., the assignee of the present invention.

As will be evident to those of ordinary skill in the art, the pressure reducer 37 operates in a standard manner such that breathing air flows from the cylinder 38 through a channel 50 formed in the center of the piston 53 in the pressure reducer 37. Once the pressure of the air below the piston 53 equals the spring 56 force, the inlet is closed and a charge of air at approximately 155 psi is held in the line until the transfer valve 31 opens allowing breathing air from the reducer 37 to pass to the mask-mounted regulator 19. As will be evident to those of ordinary skill, a pressure relief valve 39 venting to atmosphere is provided to protect against failure of the reducer 37 causing air at cylinder pressure to escape.

Once the hose line air is restored to normal pressure, the pressure from the hose line 9 that is communicated to the first poppet valve 22 will eventually move the poppet 25 to the right with respect to FIG. 1 thereby shutting off the flow through the 1000 cc/min. flow restrictor 41. With the outlet through the 1000 cc/min. flow restrictor 41 closed, the air flow through the 250 cc/min. flow restrictor 34 will eventually move the transfer poppet 22 valve back to its closed position thereby shutting off the flow from the pressure reducer 37 to the breathing mask 16.

While the invention has been described in connection with certain embodiments, it is not intended to limit the scope of the invention to the particular forms set forth, but, on the contrary, it is intended to cover such alternatives, modifications, and equivalents as may be included within the spirit and scope of the invention as defined by the appended claims.

What is claimed is:

1. A breathing gas system comprising:
   a primary breathing gas source;
   a primary gas delivery passageway for conveying breathing gas at a first operating pressure, the passageway in fluid communication with the primary breathing gas source and a breathing mask;
   a check valve disposed in the primary gas delivery passageway;
   a first valve responsive to primary breathing gas pressure, the first valve having a chamber in fluid communication with the primary gas delivery passageway, the first valve having a first valve passageway capable of alternating between an open and closed configuration, in the open configuration the first valve passageway is in fluid communication with an inlet to a first flow restrictor leading to a vent;
   a second valve responsive to primary breathing gas pressure, the second valve having a chamber disposed in fluid communication with the outlet of a second flow restrictor, the second flow restrictor having an inlet in fluid communication with the primary gas delivery passageway, the chamber also disposed in fluid communication with the passageway in the first valve, the second valve having a passageway capable of alternating between an open and closed configuration, in the open configuration the passageway is in fluid communication with a secondary breathing gas source and is in fluid communication with the breathing mask;
   the secondary breathing gas source capable of delivering secondary breathing gas at a second operating pressure; and,
   wherein the first and second valves are normally closed by the pressure of the primary breathing gas until a reduction of the primary breathing gas pressure causes the first valve to open, the opening of the first valve resulting in the primary breathing gas flowing to the vent, the venting of the primary breathing gas from the chamber of the second valve causing the second valve to open which allows secondary breathing gas to flow to the breathing mask.

2. The system of claim 1, wherein the second operating pressure is greater than the first operating pressure.

3. The system of claim 1, wherein the secondary air source comprises a compressed gas cylinder.

4. The system of claim 1, wherein the breathing mask includes a respiration on demand valve.

5. The system of claim 1, further comprising an alarm responsive to increased gas pressure.

6. The system of claim 5, wherein the alarm is mounted in the breathing regulator.

7. The system of claim 1, wherein the second valve is opened when the gas pressure on the back side of the second valve falls below a predetermined level.

8. The breathing system of claim 1, wherein the first valve is a poppet valve.

9. The breathing system of claim 1, wherein the second valve is a poppet valve.

10. The breathing system of claim 1, wherein the first flow restrictor has a greater flow rate than the second flow restrictor.

11. The breathing system of claim 1, wherein the first flow restrictor has a flow rate of about 1,000 cc/min.

12. The breathing system of claim 1, wherein the second flow restrictor has a flow rate of about 250 cc/min.

13. The breathing system of claim 1, wherein the first operative pressure is about 80 to 110 psi.

14. The breathing system of claim 1, wherein the second operative pressure is about 140–160 psi.

15. The breathing system of claim 1, wherein the system resets automatically when pressure from the hose line that is communicated to the first valve causes the first valve to close thereby shutting off flow to the first flow restrictor, the shutting off of flow to the first flow restrictor causing pressure to build up on the back side of the second valve causing the second valve to close.

16. A breathing gas system comprising:
  a primary cylinder containing breathing gas, the primary cylinder being disposed in fluid communication with a primary cylinder regulator for reducing the cylinder gas pressure to a first operating pressure;
  a primary gas delivery passageway for conveying breathing gas at the first operating pressure, the passageway in fluid communication with an outlet of the primary regulator and in fluid communication with a breathing mask;
  a check valve disposed in the primary gas delivery passageway;
  a first valve responsive to primary breathing gas pressure, the first valve having a chamber in fluid communication with the primary gas delivery passageway, the first valve having a first valve passageway capable of alternating between an open and a closed configuration, in the open configuration the first valve passageway is in fluid communication with an inlet to a first flow restrictor leading to a vent, the first valve having a spring-biased poppet that is normally closed by gas pressure at the first operating pressure such that if the pressure decreases below a predetermined value, the first valve opens due to the force of the spring;
  a second valve responsive to primary breathing gas pressure, the second valve having a chamber disposed in fluid communication with the outlet of a second flow restrictor, the second flow restrictor having an inlet in fluid communication with the primary gas delivery passageway, the chamber also disposed in fluid communication with the passageway in the first valve, the second valve having a passageway capable of alternating between an open and closed configuration, in the open configuration the passageway is in fluid communication with a secondary breathing gas source and is in fluid communication with the breathing mask; the secondary breathing source comprising an escape cylinder mounted on the user capable of delivering a secondary breathing gas at a second operating pressure; and,
  wherein the first and second valves are normally closed by the gas pressure of the primary breathing gas source until a reduction of the primary breathing gas pressure causes the first valve to open, the opening of the first valve causing the primary breathing gas to flow to the vent, the venting of the primary breathing gas from the chamber of the second valve causing the second valve to open such that secondary breathing gas flows from the secondary breathing source to the breathing mask.

17. The system of claim 16, wherein the second operating pressure is greater than the first operating pressure.

18. The system of claim 16, wherein the breathing mask includes a respiration on demand valve.

19. The system of claim 16, further comprising an alarm responsive to increased gas pressure.

20. The system of claim 19, wherein the alarm is mounted in the breathing regulator.

21. The system of claim 16, wherein the second valve is opened when the gas pressure on the back side of the second valve falls below a predetermined level.

22. The breathing system of claim 16, wherein the first valve is a poppet valve.

23. The breathing system of claim 16, wherein the second valve is a poppet valve.

24. The breathing system of claim 16, wherein the first flow restrictor has a greater rate than the second flow restrictor.

25. The breathing system of claim 16, wherein the first flow restrictor has a flow rate of about 1,000 cc/min.

26. The breathing system of claim 16, wherein the second flow restrictor has a flow rate of about 250 cc/min.

27. The breathing system of claim 16, wherein the first operative pressure is about 80 to 110 psi.

28. The breathing system of claim 16, wherein the second operative pressure is about 140–160 psi.

29. A breathing gas system, comprising:
  a primary breathing gas cylinder having a primary regulator for reducing the cylinder pressure to a first operating pressure;
  a primary gas delivery passageway for conveying breathing gas at the first operating pressure from the primary gas cylinder to an on demand regulator operatively associated with a breathing mask;
  a check valve disposed in the primary gas delivery passageway;
  a first valve responsive to primary breathing gas pressure, the first valve having a chamber in fluid communication with the primary gas delivery passageway, the first valve having a first valve passageway capable of alternating between an open and a closed configuration, in the open configuration the first valve passageway is in fluid communication with an inlet to a first flow restrictor leading to a vent, the first valve having a spring-biased poppet that is normally closed by gas pressure at the first operating pressure such that if the pressure decreases below a predetermined value, the first valve opens due to the force of the spring;
  a second valve responsive to primary breathing gas pressure, the second valve having a chamber disposed in fluid communication with breathing gas from the primary gas delivery passageway through a second flow restrictor and in fluid communication with an inlet to the first valve passageway, the second valve having a second valve passageway in fluid communication with an outlet of a pressure reducer and in fluid communication with the demand-type regulator mounted on the mask, the second valve having an open and a closed configuration, the gas pressure from the primary gas delivery passageway causing the valve to remain in the closed position, the valve capable of moving to the open position in response to a reduction in the gas pressure within the chamber, the opening of the second valve causing secondary breathing gas to flow to the regulator on the breathing mask, the check valve preventing secondary breathing gas from exiting through the primary gas delivery passageway.

* * * * *